United States Patent [19]

Klainer et al.

[11] Patent Number: 5,354,825

[45] Date of Patent: Oct. 11, 1994

[54] SURFACE-BOUND FLUORESCENT POLYMERS AND RELATED METHODS OF SYNTHESIS AND USE

[76] Inventors: Stanley M. Klainer, 20 Belinda Ct., San Ramon, Calif. 94583; David R. Walt, 12 Milk St., Lexington, Mass. 02173; Amos J. Gottlieb, 1650 Haight St., San Francisco, Calif. 94113

[21] Appl. No.: 116,878

[22] Filed: Sep. 7, 1993

Related U.S. Application Data

[60] Continuation of Ser. No. 848,569, Mar. 9, 1992, abandoned, which is a division of Ser. No. 506,430, Apr. 9, 1990, abandoned, which is a continuation of Ser. No. 4,339, Jan. 16, 1987, abandoned, which is a continuation-in-part of Ser. No. 720,749, Apr. 8, 1985, abandoned.

[51] Int. Cl.$^5$ ............................................. C08F 224/00
[52] U.S. Cl. ................................... 526/268; 526/270; 526/312; 428/500; 128/634; 422/68.1; 436/172; 250/461.1; 252/301.32; 252/301.35; 252/408.1; 252/700
[58] Field of Search ................... 252/301.32, 301.35, 252/408.1, 700; 250/461.1; 436/172; 422/68.1; 128/634; 526/268, 270, 312; 428/500

[56] References Cited

U.S. PATENT DOCUMENTS

| | | | |
|---|---|---|---|
| 4,803,049 | 2/1989 | Hirschfeld et al. | 422/58 |
| 4,812,532 | 3/1989 | Stolowitz | 525/420 |
| 5,252,494 | 10/1993 | Walt | 436/528 |

FOREIGN PATENT DOCUMENTS

| | | |
|---|---|---|
| 106086 | 5/1974 | Fed. Rep. of Germany. |
| 3343636A1 | 2/1983 | Fed. Rep. of Germany. |
| 49-62589 | 6/1974 | Japan. |

OTHER PUBLICATIONS

Munkholm et al. "Polymer Modification of Fiber Optic Chemical Sensors as a Method of Enhancing Fluorescence Signal for pH Measurement" 1986.
Saari et al., *Anal. Chem.* 54: 821–823 (1982).
Abstract JP 49062589.

*Primary Examiner*—John C. Bleutge
*Assistant Examiner*—Margaret W. Glass
*Attorney, Agent, or Firm*—Reed & Robins

[57] ABSTRACT

A fiber optic sensing device for measuring a chemical or physiological parameter of a body fluid or tissue is provided. To one end of the fiber is attached a polymer including a plurality of photoactive moieties selected from the group consisting of chromophores and lumophores, the photoactive moieties spaced apart so as to minimize chemical or physical interaction therebetween while optimizing the density of photoactive moieties. In one embodiment, a polymer chain is covalently bound to photoactive moieties through functional groups such as esters, amides, or the like. In a second embodiment, a polymer chain is inherently fluorescent and is formed from at least one monomeric unit. These devices are particularly useful as pH and oxygen sensors.

11 Claims, No Drawings

SURFACE-BOUND FLUORESCENT POLYMERS AND RELATED METHODS OF SYNTHESIS AND USE

CROSS-REFERENCE TO RELATED APPLICATION

This application is a continuation of U.S. patent application Ser. No. 07/848,569, filed Mar. 9, 1992 now abandoned, which was a divisional of U.S. patent application Ser. No. 07/506,430, filed Apr. 9, 1990, now abandoned, which was a continuation of U.S. patent application Ser. No. 07/004,339, filed Jan. 16, 1987, now abandoned, which was a continuation-in-part of U.S. patent application Ser. No. 06/720,749, filed Apr. 8, 1985, also abandoned.

FIELD OF THE INVENTION

This invention relates generally to the use of optical fibers for measuring various chemical and biochemical parameters in fluid or body tissue.

BACKGROUND OF THE INVENTION

The use of optical fibers for such analytic purposes is known and described, for example, in Hirschfeld, U.S. Pat. No. 4,577,109, entitled "Remote Multi-Position Information Gathering System and Method." Such techniques are also described by F. P. Milanovich, T. B. Hirschreid, F. T. Wang, S. M. Klainer, and D. Walt in "Novel Optical Fiber Techniques for Medical Application," published in the Proceedings of the SPIE 28th Annual International Technical Symposium on Optics and Electrooptics, Volume 494.

Briefly summarizing the method of the prior art, a sensor consisting typically of a fluorescent dye is attached to the distal end of an optical fiber, preferably of diameter suitable for in vivo application. Light of a suitable wavelength, from an appropriate source, is used to illuminate the distal end of the optical fiber, visible light, for example, having a wavelength typically between about 400 and 800 nm. The light is propagated along the fiber to its distal end. A fraction of the light is reflected at the fiber-liquid interface and returns along the fiber. A second fraction of the light is absorbed by the fluorescent dye, and light is then emitted therefrom in a band centered usually but not always at a longer wavelength. The intensity of this band is dependent upon the interaction of the dye with the property or substance measured in the body fluid or tissue. This fluorescent light is also propagated along the return path of the fiber and measured using suitable optical equipment. The ratio of the wavelengths is determined and the parameter of interest measured.

Fluorescent molecules have been attached to the distal end of an optical fiber or to a separate piece of glass, e.g., a glass bead, by a technique which is used in the immobilization of enzymes. See *Methods of Enzymology*, vol. XLIV, Ed. Klaus Mosbach, Academic Press. pp. 134–148 (1976). A fundamental problem encountered with such a technique has been the failure to provide sufficient amounts of indicator at the distal end of the fiber. The prior art describes two primary approaches to the problem. In the first of these, a porous substrate is used so that more surface area is available to which indicator moieties may bind, while in the second, as described, for example, in U.S. Pat. No. 4,269,516 to Lubbers et al., indicator is provided in solution form, which solution is separated from the external environment by a membrane.

In the former procedure, a glass surface, for example the distal end of an optical fiber (or a glass bead which is subsequently attached to the fiber), is treated so that it is porous. It is then reacted with a suitable agent such as 3-aminopropyltriethoxy silane, and a series of reactions is carried out culminating in the covalent attachment of a biologically and/or chemically active molecule, e.g., a fluorescent species, to the surface of the glass. These reactions may be represented as follows:

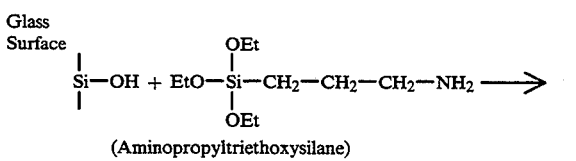

Now representing the silanized glass (referred to also hereinafter as aminoalkyl glass or fiber) as

|—NH₂ the next step is realized by reacting a fluorophore such as fluorescein isothiocyanate dissolved in an aprotic solvent with the aminoalkyl fiber

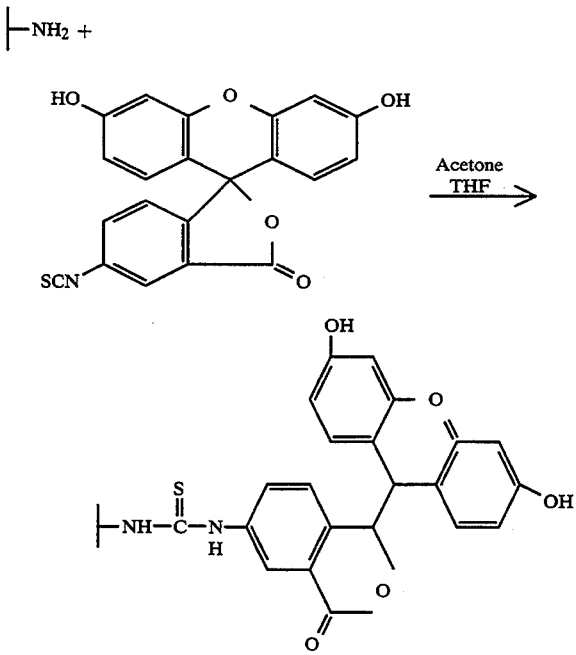

and performing the remaining conventional washing and purification steps.

A dye immobilized on glass in this manner is pH-sensitive in the physiological range and is relatively stable. However, to achieve a satisfactory degree of response, it has been necessary to employ porous glass, that is, a special alkali borosilicate glass which has been heat treated to separate the glass into two phases. Typically, the phase which is rich in boric acid and alkali is leached out with acid to leave a porous, high-silica structure. The porous structure is then silanized and treated with the desired fluorescent species. The resulting treated glass is then attached to the distal end of an optical fiber. Porous glass provides more surface area available for silanizing and thus many more fluorescent molecules can be attached.

However, this technique is difficult to carry out. The most practical way to accomplish the intended result is to provide a bead of porous glass, silanize it, react it with the fluorescent species, and then attach the glass bead to the distal end of an optical fiber. This attachment is difficult to effect because of the small size of the beads and the ease with which the pores in the glass are occluded.

The technique of using a solution behind a membrane also suffers from serious drawbacks. Most importantly, the phenomena of concentration quenching comes into play, which severely limits the amount of dye that can be in close proximity to the end of the fiber. Where fluorescent dyes are present in concentrations higher than about $10^{-3}$M, for example, concentration quenching occurs and results in a substantial loss of accuracy. Several processes are believed to be responsible for concentration quenching: (1) the increased probability of self-absorption at higher densities or concentrations of fluorophores; (2) formation of dimers or higher aggregates which are normally less fluorescent than the monomer; and (3) reaction of excited molecules with ground state molecules to form excimers, which again have emission spectra quite different from the monomer spectrum. See, e.g., Guilbault, *Practical Fluorescence*, New York: Marcel Dekker, Inc., 1973. Similar problems arise in the case of absorbing dyes, where exciton interaction—that is, interaction of dipoles on neighboring groups or molecules—is a factor at higher densities. See Birks, *Photophysics of Aromatic Molecules*, London: Wiley & Sons, 1970.

SUMMARY OF THE INVENTION

Accordingly, it is an object of the present invention to overcome the aforementioned disadvantages of the prior art.

It is another object of the invention to provide a fiber optic sensing device, comprising an optical fiber to one end of which is attached a polymer including a plurality of photoactive moieties spaced apart from each other at a preselected distance.

It is still another object of the invention to provide such a device wherein the preselected distance is sufficient to minimize chemical or physical interaction between the photoactive moieties while optimizing the density thereof.

It is yet another object of the invention to provide such a device wherein the photoactive moieties are covalently attached to the polymer through functional groups, such as through ethers, amides, or the like.

It is a further object of the invention to provide such a device wherein the polymer is inherently fluorescent and includes at least one monomer unit which is itself photoactive.

It is still a further object of the invention to provide such a device wherein the inherently fluorescent polymer is quenchable by oxygen.

It is another object of the invention to provide a method of making fiber optic sensing devices, comprising attaching a plurality of monomeric units, sequentially or as a preformed polymer, to an optical fiber tip, wherein at least a fraction of the monomeric units include photoactive moieties.

Additional objects, advantages and novel features of the invention will be set forth in part in the description which follows, and in part will become apparent to those skilled in the art on examination of the following, or may be learned by practice of the invention.

In one aspect of the invention, a fiber optic sensing device is provided, comprising a fiber to one end of which is attached a polymer including a plurality of photoactive moieties. The photoactive moieties, which may be chromophores or lumophores are positioned along the polymer in such a way as to optimize the distance between the moieties. That is, chemical or physical interaction (e.g., concentration quenching, exciton interaction, steric interference) is minimized while the density of photoactive moieties is optimized. The high density of photoactive moieties achieved with the present invention provides an apparatus of substantially increased sensitivity.

The photoactive moieties may be attached as side groups. i.e. pendant to the main polymer chain. In such a case, each photoactive moiety is attached through one bond to the polymer backbone. In an alternative embodiment of the invention, in which the polymers are designated "inherently fluorescent," each photoactive moiety is in the backbone of the polymer, i.e. is bound to the remainder of the polymer through two or more bonds.

In another aspect of the invention, a method of forming a fiber optic device is provided. The method involves either sequential attachment of labeled monomer units to a fiber optic tip, or, alternatively, attachment (covalent or otherwise) of a preformed polymer to a fiber optic tip: the preformed polymer may be labeled with photoactive moieties before attachment or after.

Potential uses of the device include, inter alia, use as a pH sensor, an oxygen sensor, an electrolyte sensor and a blood gas sensor.

DETAILED DESCRIPTION OF THE INVENTION

As used herein, "photoactive" moieties are molecular species which undergo a detectable change in electronic configuration in response to interaction with light. In the present invention, the detectable change corresponds to one or more chemical or physiological parameters.

"Chromophores" are atoms or groups of atoms that serve as units in light absorption. For example, a chromophore includes the electronic substructure of a dye that absorbs light and thereby causes the material to be colored. A change in the environment of a chromophore can change the amount of light absorbed at a particular wavelength or the amount of light absorbed over a range of wavelengths. Examples of chromophores useful herein include cresol red and phenol red. Suitable chromophores also include lumophores such as pyrenes, perylenes and their derivatives, and other paracyclic aromatic compounds.

"Lumophores" are atoms or groups of atoms that serve as units in light emission. All compounds which are capable of undergoing fluorescence or phosphorescence include a lumophore.

"Chemical or physical interaction" between the photoactive moieties of a polymer, as used herein, includes any interaction which (1) changes the electronic absorption spectrum obtained; (2) changes the electronic emission spectrum obtained; (3) changes the quantum yield of emission; (4) interferes with the accurate measurement of particular chemical or physiological parameters in a sample or (5) destabilizes the polymer structure.

A "substantially nonporous" material is a material having a porosity less than about 5% (vol./vol.).

"Inherently fluorescent" polymers, as used herein, are polymers formed from one or more photoactive monomer units, so that photoactive moieties are actually present within the polymer backbone so that each is bound to the remainder of the polymer chain through two or more bonds. This is in contrast to polymers in which the photoactive moieties are pendant to the polymer chain, where each is bound through only one bond to the remainder of the polymeric structure.

The optical fiber of the present invention is typically between about $50\mu$ and about $600\mu$ in diameter. In a preferred embodiment, the sensing device is useful for in vivo applications, for example to measure pH or oxygen concentration, in which case the diameter should be between about $50\mu$ and about $250\mu$.

The fiber may be comprised of virtually any material so long as it is an optical conductor at the wavelengths of interest. For example, the fiber may be an organic material such as polymethylmethacrylate, polystyrene, polymethylphenyl siloxane or deuterated methyl methacrylate, or it may be an inorganic material such as glass. As noted earlier, successful use of substantially nonporous materials in this application—that is, to give a highly sensitive device—represents a significant improvement in the art.

The polymer which is attached to the fiber tip can be any stable polymer which can be derivatized so as to contain photoactive moieties. In addition, the polymer must be optically transparent both to exciting light, i.e. light directed through the fiber into the polymer, and to light emitted from the photoactive moieties attached thereto. Examples of polymers suitable for use herein include polyacrylamides, polylysines, polymethacrylates, polyurethanes, polyethers, and polysiloxanes such as polydimethyl and polymethylphenyl siloxane. The polymer chain is preferably less than about 200 monomer units in length, to ensure that substantially all photoactive moieties are maintained fairly close to the fiber tip.

The polymer may be attached to the fiber in a number of ways. In a preferred embodiment, the polymer is attached to the fiber covalently, typically through an aminoalkyl or other linking group (see Example 4). Suitable linking groups for glass and other fibers may be prepared from the following: diaminoalkanes, diaminoaryl compounds, diisothiocyanate-substituted aryl compounds, alkyldialdehydes, arylalkyl dialdehydes, arylalkyldiamines, alkyl dicarboxylic acid derivatives, arylalkyl decarboxylic acid derivatives, aryl dicarboxylic acid derivatives, alkyl diols, aryl diols, arylalkyl diols, and the like. Alternatively, the polymer may be attached to the polymer by adsorption or electrostatic interaction. In the latter case, the polymer is attached to the fiber by forming a salt of the polymer and a linking group on the fiber.

Unless the polymer is of the "inherently fluorescent" type, it must be provided with areas of reactivity so that photoactive moieties can bind to the polymer backbone. The photoactive moieties may bind directly to the polymer backbone or may bind to the polymer through functional groups such as ethers, amines, amides including acrylamides, esters, alkyl moieties having from about two to about twenty-two carbon atoms, arylalkyl, etc.

Suitable photoactive moieties for use herein include chromophores, lumophores and combinations thereof. Chromophores include, for example, cresol red and phenol red. Lumophores include both fluorophores and phosphors. Examples of suitable fluorophores for use herein are fluorescein, perylene, pyrene and their derivatives. An examples of a suitable phosphor is rose bengal.

The reactive areas on the polymer are distributed along the polymer chain such that the photoactive moieties are spaced apart by at least about 4 Å, that is, the distance between photoactive moieties is determined by the relative frequency of the species in the polymer backbone. This frequency can be achieved during preparation of the polymer by diluting the photoactive moiety, i.e. by introducing a nonphotoactive comonomer during polymerization. Alternatively, with a preformed polymer having reactive functional groups to which photoactive moieties will bind, the frequency of these moieties can be controlled by dilution during the reaction attaching the pendant moieties or by using a nonphotoactive moiety which can compete for binding to the functional groups on the polymer chain.

In some cases, depending on the environment and on the photoactive moieties selected, i.e. where there is a potential for interaction at a greater distance, spacing of at least about 14 Å is preferred. The distance factor is key to the present invention, as the distance between photoactive moieties is carefully preselected so as to minimize chemical or physical interaction therebetween, while optimizing the density thereof close to the fiber tip. The inventors herein have demonstrated that, generally, the amount of light recaptured by the fiber from the photoactive moieties is strongly dependent on the density of these groups. The strength of the signal ultimately generated is also dependent on the distance of the active moieties from the end of the fiber to these groups. Thus, and as accomplished by the present invention, it is advantageous to have a very high density of photoactive moieties at the fiber tip, as close to the end of the fiber as possible.

Generally, the fiber tip will be provided with a plurality of polymer chains all similarly bonded to the fiber. The spacing of photoactive moieties is then controlled not only along a single polymer chain but also between polymer chains. This is accomplished by controlling the number of polymer chains attached to a given area of the fiber tip, for example, by minimizing the number of attachment sites on the substrate or by reacting some of the sites with nonphotoactive polymer chains.

A primary use of the above-described sensing device, a preferred embodiment herein, is as a pH sensor. The fiber tip is placed into contact with a fluid or tissue, light is directed along the fiber toward the fiber-sample interface so that photoactive species are caused to fluoresce, and the ratio of fluorescence to reflected light is determined. This ratio changes with pH in a predictable fashion; thus, pH may be determined by interpolating along a curve prepared from known pH/ratio points.

In an alternative embodiment of the invention, a fiber optic sensing device is provided which comprises a fiber tip to one end of which is attached an inherently fluorescent polymer. The polymer has as part of its molecular structure a chromophore, lumophore or the like, i.e. it is actually formed from one or more photoactive monomer units.

Such a device provides a number of advantages: first, as with the embodiment described earlier, a very high optical density may be achieved without interfering effects such as concentration quenching. This allows for a very thin, yet highly absorbing, polymer layer. The thinness of the polymer layer causes an increase in the amount of emitted light which enters the fiber and allows, also, for a mechanically sturdy configuration. A second advantage is that with inherently fluorescent polymers, as with the polymers having pendant photoactive moieties, there is no separate dye which can migrate out of the polymer matrix. This promotes long-term stability of the device and allows the material to be used in contexts where dye toxicity could otherwise be a problem.

The inherently fluorescent polymers are prepared by reaction of a photoactive moiety with a reactive monomeric species under polymerization conditions. The photoactive moieties may be introduced within a straight-chain polymer or as cross-linking functionalities in a cross-linked polymer (see Examples 16 and 17). Suitable photoactive moieties are as described earlier, and particularly suitable photoactive moieties for use in the inherently fluorescent polymer application are derivatives of pyrene. Preferred polymers include polycarbonamides, polyurethanes, polyamides, polyimides, polyesters, and polysiloxanes such as polymethylsiloxanes. polymethylphenylsiloxanes and the like.

A preferred use of the fiber optic sensing device which incorporates an inherently fluorescent polymer at the optical fiber tip is as an oxygen sensor. In such an application, the photoactive moieties incorporated in the polymer are fluorescent species which are quenchable by oxygen. The device is constructed so that fluorescence emission varies with (typically is inversely related to) the oxygen concentration of its environment, which may be gaseous or aqueous (e.g., blood).

The present invention also encompasses a method of attaching labeled polymeric species—inherently fluorescent or otherwise—to a fiber optic tip. In one embodiment, the method involves sequential addition of monomer or oligomer species to a linking group present on the fiber. At least a fraction of these species is photoactive. In another embodiment, the method involves attachment of a preformed polymer to the fiber tip, which polymer may be labeled with photoactive moieties prior to attachment or after. The attachment of the preformed polymer may be covalent, or it may be effected by adsorption or electrostatic binding.

In developing the device of the present invention, the inventors herein discovered a new and useful fluorescent compound attachable in a simple, one-step reaction to a polymer chain. This compound is a fluorophore having an acryloyl substituent on an aromatic ring, and in one embodiment is given by the following structure

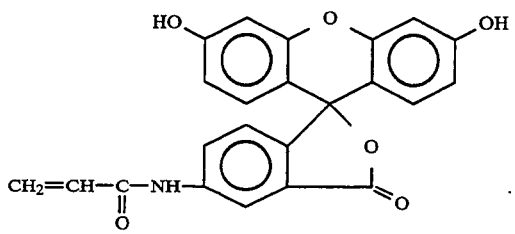

It will be apparent to those skilled in the art that the compound may be further substituted on the aromatic rings, e.g., with halogen substituents or lower alkyl or alkoxy groups. Such a fluorescent acrylamide is then polymerizable (with or without nonfluorescent acrylamide monomers) in the presence of a catalyst such as 2,2'-azobisisobutyronitrile to form fluorescent polymers having the structure

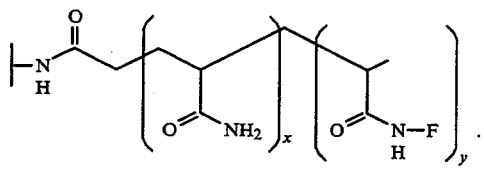

In the above structure, x and y represent the number of nonfluorescent and fluorescent monomer units in the polymeric structure, respectively, and are selected so as to provide the requisite spacing between photoactive moieites. Typically, x and y each range from about 1 to about 200, and the sum of x and y is also, typically, less than about 200. F represents the major portion of the molecule given by

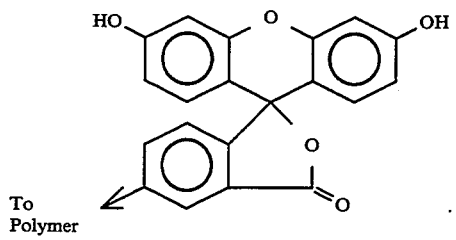

It is to be understood that while the invention has been described in conjunction with specific embodiments thereof, that the foregoing description as well as the examples which follow are intended to illustrate and not limit the scope of the invention, which is defined by the appended claims. Other aspects, advantages and modifications within the scope of the invention will be apparent to those skilled in the art to which the invention pertains.

EXAMPLE 1

Preparation of Acid Glass

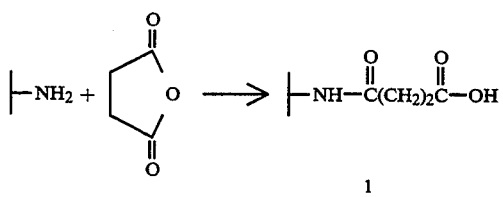
1

In 1 and generally hereinafter, the group —NH— is derived from the primary amino group of the aminoalkyl glass.

The acid glass 1 was prepared as follows: Succinic anhydride (Aldrich, 3.0 g) was dissolved in anhydrous tetrahydrofuran (THF) (100 ml). Silanized glass, i.e. aminoalkyl glass (Pierce Chemical, 1 g), was added and the solution was refluxed for four hours. The glass was then washed with 30 ml of acetone and dried in vacuo at 25° C. for thirty minutes.

EXAMPLE 2

Preparation of Acid Chloride Glass

The acid glass of Example 1 was treated with $SOCl_2$ as follows: A 10% solution of thionyl chloride (Aldrich) in dry chloroform was prepared. 0.5 g of acid glass was added to 20 ml of the thionyl chloride solution and refluxed for four hours. The glass was then rinsed with chloroform and dried under vacuum for thirty minutes.

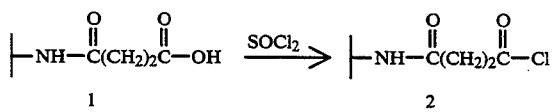

EXAMPLE 3

Preparation of N-Hydroxy Succinic (NHS) Glass

The acid chloride glass of Example 2 was reacted with N-hydroxysuccinimide as follows:

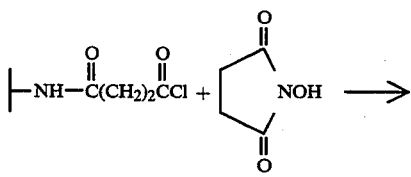

The reaction was carried out as follows: 3.8 g of N-hydroxysuccinimide (Aldrich) and 4.45 ml of triethylamine (Aldrich) were added to 50 ml of anhydrous stirred chloroform. This solution was then cooled to 0° C. Acid chloride glass was added and the suspension was stirred for an additional forty minutes. The temperature of the suspension was maintained at 0° C. during this stirring period. The glass was filtered, and the beads were washed with chloroform and dried in vacuo at 25° C. for thirty minutes.

The purpose of treating the acid chloride glass with N-hydroxy succinimide was to protect the treated glass from hydrolysis in subsequent treatment.

EXAMPLE 4

Treatment of NHS Glass with Triethylenetetramine (TET)

The NHS glass from Example 3 is added with stirring to a mixture of 50 ml of anhydrous chloroform and 8 ml of triethylenetetramine (Aldrich). The glass mixture is stirred for one hour, and the beads are then filtered, washed with chloroform and dried in vacuo at 25° C. for thirty minutes. The reaction may be represented as

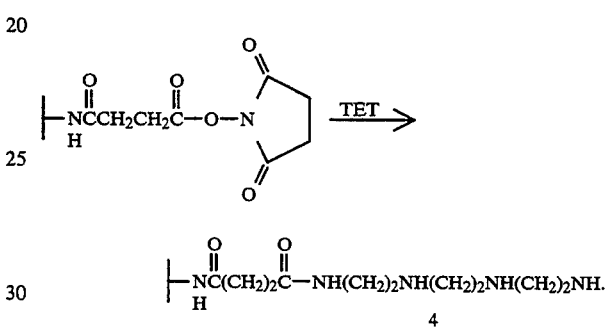

The treated, aminoalkyl glass 4 has numerous nitrogen functionalities to which fluorescent groups may be attached.

EXAMPLE 5

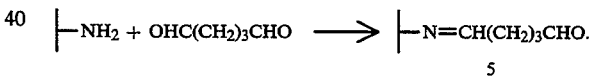

Glutaraldehyde glass (represented by structure 5) was prepared as follows. A solution of 25% glutaraldehyde was diluted to 2.5% in 0.1M $Na_3PO_4$, pH 7, to 50 ml. The aminoalkyl glass prepared in the preceding Example was immersed for one hour and then rinsed with deionized water.

EXAMPLE 6

Glutarylchloride (glut-Cl) Glass

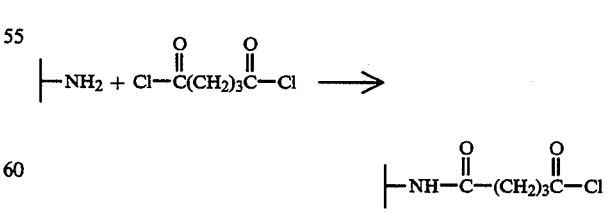

2.5 ml of glutaryl dichloride [source?] was diluted to 10 ml in anhydrous THF. Aminoalkyl glass (400 mg) as prepared in Example 4 was immersed for one hour in this solution and then rinsed with dry acetone.

EXAMPLE 7

Attachment of a Fluorescent Polymer to Aminoalkyl Glass (a) Preparation of N-substituted acrylamide derivative of fluorescein: Two hundred mg of fluorescein amine 7 (Aldrich) were dissolved in a mixture of 1.0 ml anhydrous dimethyl formamide and 25 ml anhydrous chloroform, followed by addition of 0.56 ml of acryloyl chloride (Aldrich). The reaction mixture was stirred and maintained at a temperature of 25° C. After sixty minutes, the pH of the reaction mixture was found to be about 3, indicating formation of HCl and thus reaction of the fluorescein amine with the acryloyl chloride. The solvent was stripped off in vacuo leaving an amber oil. The product was presumed to have the formula 8.

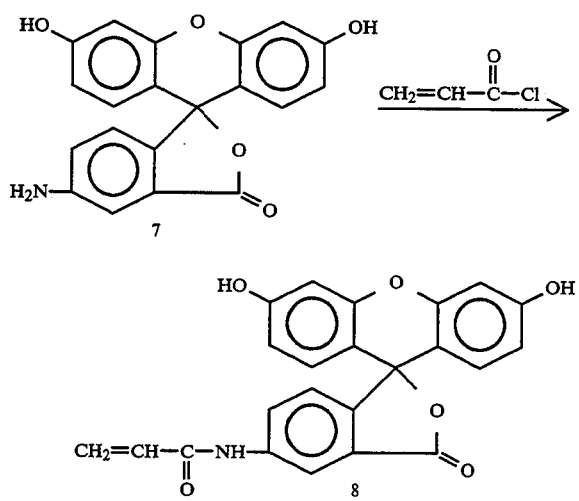

(b) Copolymerization of Acrylamide and 8 with Aminoalkyl Glass: 400 ml of 8 were dissolved in 30 ml tetrahydrofuran together with 1 g acrylamide and 10 mg of 2,2'-azobisisobutryo nitrile (AIBN) (Polysciences) as catalyst. Aminoalkyl glass in the form of a fiber tip (prepared as in Example 4) was activated in 1 ml acryloyl chloride for one hour, immersed in the acrylamide solution, and heated at 50° C. for twenty hours. A copolymer of 8 and acrylamide linked to the aminoalkyl glass resulted in the structure given by 9, wherein x and y indicate the numbers of the respective monomer units.

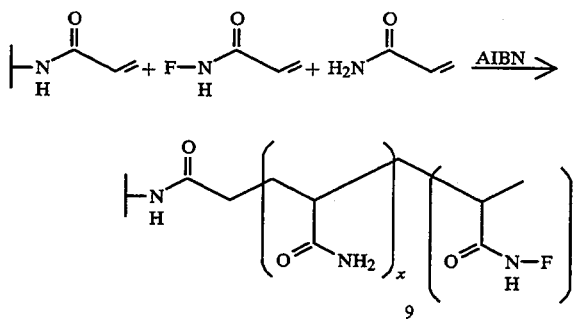

The monomer units in all likelihood occur in some more or less random order. The pendant group F is derived from 8; i.e., it is the group 8a.

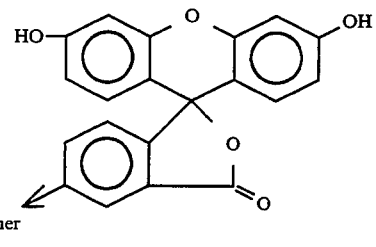

(c) Testing of Fiber Tip 9: The fiber tip 9 was tested as a pH sensor by immersion first in a buffer solution at pH 6.8 and then in a second buffer solution at pH 7.8. The ratio of the intensity of light resulting from fluorescence to that of the reflected light was found to be 0.81 at the lower pH and 1.1 at the higher pH.

(d) Comparison with a Porous Glass Bead to which FITC is Directly Attached: A porous glass bead (OD=177$\mu$, average pore size=500), was glued to the end of an optical fiber and activated by treatment with aminopropyl triethoxy silane (Petrarch) 10 wt. % aqueous solution, pH 3.45, treatment time sixty minutes). Due to the porous nature of the glass, many aminoalkyl groups were presumed attached. The fiber was then rinsed in distilled water and air dried at 90° C.

Ten mg fluorescein isothiocyanate (FITC) (Molecular Probes) was dissolved in 5 ml acetone and the tip of the fiber described above was immersed in the solution for sixty minutes at room temperature. The fiber was rinsed with acetone, and tested as in Example 7(c) above. The ratio of the intensity of light resulting from fluorescence to that of the reflected light was found to be 0.54 at pH 6.8 and 1.29 at pH 7.8.

In example 7(c) the glass to which the fluorescent species was attached was nonporous. It was treated to append aminoalkyl groups but eliminated the tedious step of attachment of a porous bead.

The polymeric technique thus achieves a result which is similar to that achieved with porous glass, the porous glass route, however, being less desirable due to attachment problems.

EXAMPLE 8

Glass Fiber Treated with FITC

By way of further comparison, aminoalkyl glass fiber as in Example 7(b) was treated as follows: The fiber was soaked first in a solution containing 5 mg of FITC in 100 ml of acetone for one hour and then in deionized water for one hour. No observable fluorescent pH effect could be measured using the procedure of Example 7(c).

EXAMPLE 9

Glass Fiber Treated with High Molecular Weight Polylysine and FITC

A glutaraldehyde-treated aminopropyl glass fiber (prepared as in Example 5) was placed in a solution of 4 mg of 540,000 D average molecular weight ($M_w$) polylysine in 4 ml of deionized water and allowed to soak for one hour at 23° C. The fiber was then allowed to stand in a deionized water wash for one hour after which time it was treated with a solution of 5 mg FITC/100 ml acetone for one hour. Its pH-dependent fluorescence was measured. At pH 6.8 the ratio of fluorescence to reflected light was 0.11, and at pH 7.4 it was 0.21.

EXAMPLE 10

Glass Fiber Treated with Low Molecular Weight Polylysine and FITC

A glutaraldehyde-treated aminopropyl glass fiber (prepared as in Example 5) was placed in a solution of 4 mg of 4,000 D average molecular weight ($M_w$) polylysine (Polysciences) in deionized water and allowed to soak for one hour at 23° C. The fiber was then placed in a deionized water wash for one hour and immediately treated with a solution of 5 mg FITC/100 ml acetone for one hour. The fiber was then rewashed in deionized water for one hour and its pH-dependent fluorescence measured. The ratio of fluorescent to reflected light at pH 6.8 was 0.35 and at pH 7.4 was 0.52.

From the results of Examples 9 and 10, it may be concluded that the polylysine was attached covalently to the aminopropyl glass and that FITC molecules were attached covalently as pendant groups to the polylysine chains.

EXAMPLE 11

Electrostatically Bound Fluorescent Polymer

A fluorescent polymer is prepared having pendant fluorescent groups and pendant carboxyl groups. The polymer is caused to react with activated glass (i.e., the aminoalkyl glass of Example 4) having basic groups, resulting in the following:

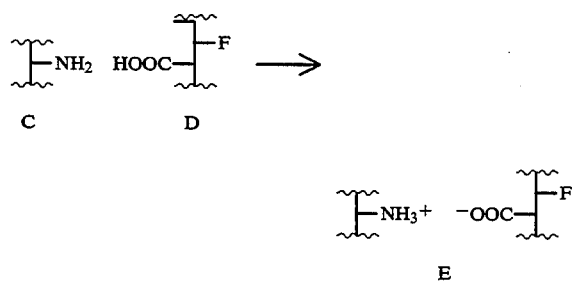

where C represents one of a multiplicity of activated groups on glass, D represents a repeating unit in the polymer described above (wherein F represents a pendant fluorescent group) and E represents the resulting salt. This may be accomplished by reacting aminopropyl glass C with a fluorescently labeled polymer D. The resulting ionic salt bridges are then stabilized by drying the product in vacuo.

EXAMPLE 12

Adsorption of a Fluorescent Polymer on an Aminoalkyl Glass Surface

A polymer having pendant fluorescent groups is prepared, e.g., a copolymer of acrylamide and the acryloyl derivative 8 of fluorescein prepared as described in Example 7(b) but in the absence of aminopropyl glass. An aminopropyl glass fiber tip is immersed in a 0.01 molar aqueous solution of this copolymer for two days. The fiber is then rinsed with chloroform for three days to remove the nonadsorbed polymer and is dried in vacuo at 25° C. for one hour.

EXAMPLE 13

Immunoassay Embodiment

In the enzyme-linked immunoassay (ELISA) technique, an enzyme is immobilized on the surface of a test tube or cuvette. See, for example, Chang, *Biochemical Applications of Immobilized Enzymes and Proteins*, Vol. 2, Plenum Press, 1977, Chapters 30–33. This technique is improved by the amplification technique of the present invention as follows.

An acetaminophen-specific antibody is treated with a one hundredfold molecular excess of acryloyl chloride, and taken into solution with deionized water to which a twofold quantity of acrylamide has been added together with a suitable amount of AIBN. An aminopropyl glass optical fiber is treated with an excess of acryloyl chloride, washed, added to the acrylated antibody/AIBN solution and warmed at a sufficient temperature to promote graft polymerization of the antibody derivative to the silica surface without denaturing the protein.

Next, an acetaminophen-alkaline phosphatase conjugate is incubated with the immobilized antibody, filtered, washed, and the unknown quantity of acetaminophen-analyte added. The residual bound enzyme activity is then measured and the quantity of acetaminophen calculated.

In the examples above, fluorescent species such as compound 8 and FITC are used and the ratio of fluorescent light to reflected light is measured. As noted, active species other than fluorescent species may be used. For example, phenol red, cresol red and neutral red may be used. These dyes change color with pH. These dyes have functional groups which are capable of reacting with functional groups of monomers and polymers and can be incorporated in polymer molecules formed in situ or in preformed polymers. The following example will serve for purposes of illustration.

EXAMPLE 14

Incorporation of Cresol Red in a Polymer Chain

Cresol red (0.038 g) is dissolved in 30 ml of chloroform. N-Bromosuccinimide (0.017 g) is added along with benzoyl peroxide (0.005 g). The solution is refluxed for one hour and allowed to cool to room temperature. The succinimide is removed by filtration and the bromomethyl cresol red is crystallized from acetic acid.

To a solution of dimethylformamide (25 ml) containing the bromoethyl cresol red derivative (0.025 g) is added a tenfold molar excess of allylamine. The reaction mixture is heated with stirring at 50° C. under argon in the dark for six hours. The reaction mixture is then cooled to room temperature and the solvent removed under high vacuum.

The reaction product of the bromomethyl cresol red and allylamine is dissolved in DMF (50 ml) together with 1 g of acrylamide and 10 mg 2,2'-azobisisobutyronitrile. Into this solution is placed aminoalkyl glass, in the form of a fiber tip, which has been previously treated with a mixture of acryloyl chloride (0.10 g), pyridine (20 ml), and N,-N'-dimethylamino pyridine (0.010 g) for two hours. The resulting amidated fiber is heated with the bromomethyl cresol red allylamine product and acrylamide is formed at the end of the fiber.

A simplified reaction scheme is as follows:

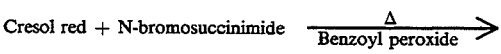

-continued

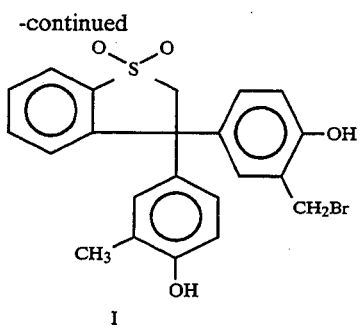

I

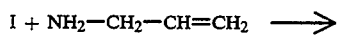

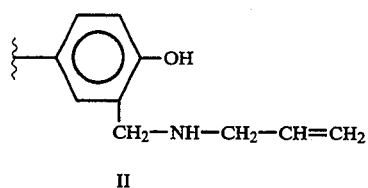

II

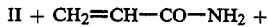

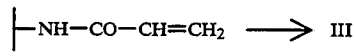

In II, the remainder of the molecule is as in I. III is the glass fiber to which a copolymer of acrylamide and II is covalently attached.

It will be apparent that a new and useful method of making optical fibers having enhanced capacity for fluorescence, etc., and new and useful optical fibers having such enhanced properties have been provided.

EXAMPLE 15

Preparation and Use of a Fluorescent Polycarbonamide

The cleaved end of a silica core step index, glass-on-glass optical fiber, was treated with a 10% solution of aminopropyltriethoxysilane in toluene overnight at 100° C. The well-rinsed fiber was inserted through a condenser attached to a flask charged with diaminodecane (137 mg), sebacoyl chloride (190 mg), perylene-3,9-dicarboxylic acid chloride (3 mg), triethylamine (107 mg) and chloroform (100 ml). The solution was refluxed, and a fluorescent polymer was allowed to form and grow from the end of the fiber. After one hour, the fiber was removed and rinsed.

When properly filtered blue light was launched into the fiber, fluorescent green light could be collected (after it had traveled back along the optical fiber) by use of a dichroic mirror and appropriate optical filter. The intensity of the green light was inversely related to the amount of oxygen in the environment surrounding the polymer tip. This was observed when the polymer tip was in a gaseous or aqueous environment.

EXAMPLE 16

Preparation of a Fluorescent Silicone

A sample of the diallyl ester of perylene-3,9-dicarboxylic acid (3 mg) was mixed with a 1 ml sample of a methylhydrodimethyl siloxane copolymer, and a small amount of platinum catalyst was added. Upon heating, a homogeneous fluorescent green or yellow material was formed. The intensity of the fluorescence emission of this material varies with the oxygen content of its environment. The material may be mounted at the end of a fiber by a mechanical means such as a capillary, and the fiber can then be used as an optrode.

For example, a piece of 240μ ID Celgard TM hollow porous fiber was slipped over the end of a 140μ plastic-clad silica optical fiber. A sample of the partially cured polymer was then wicked into the hollow fiber. The fiber was then heated while the polymer cured to form a solid material. The fluorescence emission from this tip, when monitored as described in Example 1, was inversely related to the oxygen concentration of its environment. This was observed in both gaseous and aqueous environments, including canine blood. This behavior could still be observed when the optical fiber had been subjected to steam sterilization.

We claim:

1. A fluorescent polymer containing x nonfluorescent monomer units having the structural formula

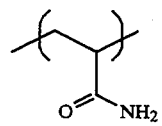

and y fluorescent monomer units having the structure

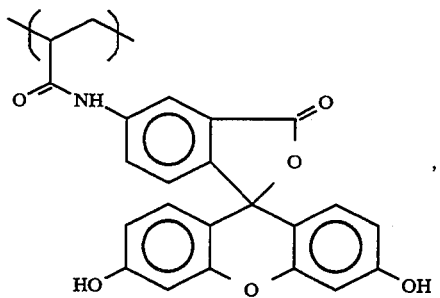

wherein x and y are integers in the range of approximately 1 to 200, and further wherein the polymer is bound to the surface of a substrate.

2. The polymer of claim 1, wherein the sum of x and y is less than about 200.

3. The polymer of claim 2, wherein the substrate is an optical fiber.

4. The polymer of claim 3, wherein the optical fiber is comprised of an organic material.

5. The polymer of claim 4, wherein the organic material is selected from the group consisting of polymethylmethacrylate, polystyrene, polymethylphenyl siloxane and deuterated methyl methacrylate.

6. The polymer of claim 3, wherein the optical fiber is comprised of an inorganic material.

7. The polymer of claim 6, wherein the inorganic material is glass.

8. A surface-bound fluorescent polymer having the structure

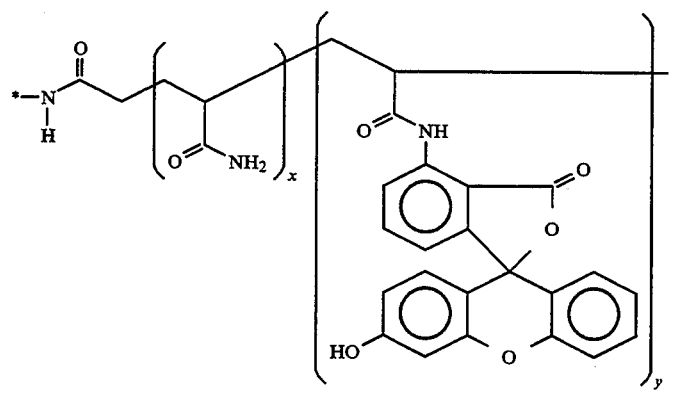

wherein:
x and y are integers in the range of approximately 1 to 200; and
* represents the point of attachment of the polymer to the surface of a substrate.

9. The surface-bound fluorescent polymer of claim 8, wherein the substrate is an optical fiber.

10. The surface-bound fluorescent polymer of claim 9, wherein the optical fiber is comprised of an inorganic material.

11. The polymer of claim 10, wherein the inorganic material is glass.

* * * * *

UNITED STATES PATENT AND TRADEMARK OFFICE
CERTIFICATE OF CORRECTION

PATENT NO. : 5,354,825
DATED : Oct. 11, 1994
INVENTOR(S) : Klainer et al.

It is certified that error appears in the above-identified patent and that said Letters Patent is hereby corrected as shown below:

On the cover page of the patent, column 1, please remove Amos J. Gottlieb's name from the list of inventors.

On the cover page of the patent, after the inventors' names, please insert the following assignment information:

--Assignee: Optical Sensors Incorporated, Eden Prairie, MN.--

Signed and Sealed this

Fourteenth Day of February, 1995

Attest:

BRUCE LEHMAN

*Attesting Officer*  *Commissioner of Patents and Trademarks*